United States Patent
Salo et al.

(10) Patent No.: US 6,278,894 B1
(45) Date of Patent: Aug. 21, 2001

(54) MULTI-SITE IMPEDANCE SENSOR USING CORONARY SINUS/VEIN ELECTRODES

(75) Inventors: Rodney W. Salo, Fridley; V. A. Kadhiresan, Lino Lakes; Kevin G. Nugent, Minneapolis, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/336,449

(22) Filed: Jun. 21, 1999

(51) Int. Cl.[7] .................................................. A61B 5/05
(52) U.S. Cl. ............................................................. 600/547
(58) Field of Search ................................... 600/547, 300; 607/24, 6, 8

(56) References Cited

U.S. PATENT DOCUMENTS

| | | | |
|---|---|---|---|
| 4,674,518 | * 6/1987 | Salo | 600/547 |
| 4,686,987 | * 8/1987 | Salo et al. | 607/24 |
| 5,036,849 | 8/1991 | Hauck et al. . | |
| 5,190,035 | 3/1993 | Salo et al. . | |
| 5,235,976 | 8/1993 | Spinelli . | |
| 5,501,702 | 3/1996 | Plicchi et al. . | |
| 5,540,727 | 7/1996 | Salo et al. . | |
| 5,836,976 | * 11/1998 | Min et al. | 607/6 |

FOREIGN PATENT DOCUMENTS

WO 99/13941  3/1999 (WO) .
WO 99/30777  6/1999 (WO) .

OTHER PUBLICATIONS

Geddes, et al, "Continuous Measurement of VEntricular Stroke Volume by Electrical Impendance", *Cardiovascular Research Center Bulletin*. vol. 4, No. 4, Apr.–Jun., 1996, pp. 119–131.

* cited by examiner

*Primary Examiner*—Eric F. Winakur
*Assistant Examiner*—Brian Szmal
(74) *Attorney, Agent, or Firm*—Nikolai, Mersereau & Dietz, P.A.

(57) ABSTRACT

A method and apparatus for performing impedance plethysmography on a living heart for diagnostic and therapy purposes involves placement of plural leads where at least one is disposed within a coronary vein traversing the myocardium on the left side of the heart with another lead having plural electrodes thereon disposed in the right ventricle. By appropriate selection of electrodes on the first and second leads for driving with an AC carrier signal and other such electrodes coupled to a sensing amplifier, an impedance vs. time signal can be derived that when signal processed provides useful information concerning cardiac performance. The multi-site impedance sensing has been found to yield more robust data especially in patients having CHF.

9 Claims, 5 Drawing Sheets

MULTI-SITE IMPEDANCE SENSOR USING CORONARY SINUS/VEIN ELECTRODES

BACKGROUND OF THE INVENTION

I. Field of the Invention

This invention relates generally to cardiac rhythm management apparatus incorporating impedance sensing capability, and more particularly to a multi-site impedance sensing system having one or more leads arranged to localize sensing of impedances in the left ventricular chamber.

II. Discussion of the Prior Art

The first use of electrical impedance to attempt to measure the chamber volume of the heart reported by Geddes, et al. in a paper entitled "Continuous Measurement of Ventricular Stroke Volume by Electrical Impedance", *Cardiovascular Research Center Bulletin*, Vol. 4, pp. 118–131, ©1966, involved the use of a pair of epicardial electrodes which were sewn to the surface of the left ventricle spanning its volume. A constant AC current was injected between these electrodes and the potential difference generated was used as a measure of the left ventricular volume. Converting the potential difference into electrical resistance, the group obtained calibration constants for this technique of 4.2–10.0 ml./ohm and found the calibration to be highly dependent on the individual. Because the electrodes were sutured into position, the separation was highly stable and there was very little signal artifact due to motion of the electrodes.

In 1970, in an effort to reduce the invasiveness of the technique, the same research group made similar measurements using a single multi-electrode catheter positioned in the left ventricle. They obtained similar results to the initial studies but the technique was only useful acutely due to the possibility of thrombus formation in the left heart and its attendant dangers. Subsequent research concentrated on acute catheter-based measurements in the left heart primarily because knowledge of the function of the left ventricle was considered to be more critical than the right ventricle for most patient conditions.

The first application of impedance plethysmography to an implantable device is described in Salo, et al. U.S. Pat. No. 5,190,035 which uses electrical impedance from a single multi-electrode lead positioned in the right ventricle to measure stroke volume. In its simplest implementation, this approach required a three-electrode lead. The current source was connected between the distal tip electrode and the pacemaker case and the measurement of impedance was made between the two remaining ring electrodes, which were positioned within the right ventricle. This arrangement was satisfactory for the measurement of stroke volume, since right and left ventricular stroke volumes must remain, on the average, equal. The system was relatively unpopular due to its requirement for a non-standard tripolar lead and was also unable to measure left ventricular parameters in situations (such as left bundle branch block, etc.) where the left ventricular performance can diverge from that of the right ventricle.

The requirement for a three electrode lead was addressed by the Hauck, et al. U.S. Pat. No. 5,036,894 which teaches the utilization of the pacemaker metal can and an additional electrode disposed on the device's insulating lead connector block as the two proximal electrodes. Thus, it was possible to make tetra polar impedance measurements using a standard bipolar pacing lead in the right ventricle, obviously, this configuration did not address the measurement of left ventricular parameters and was also sensitive to global impedance changes within the torso (such as respiration) due to the wide separation of sensing electrodes.

A further area of concern is the sensitivity of the lead system to motion. The heart is constantly in violent motion. During each cardiac cycle, there is inward and outward movement of septal and lateral walls, upward motion of the apex and spiral movement of the entire chamber wringing the blood out of the ventricles. In addition, the whole heart swings from the great vessels. These cardiac motions promote lead motions which result in impedance changes which are misinterpreted as changes in volume. Separating current sources and measuring electrodes can diminish the impact of this motion, by placing the measuring electrodes in regions of more uniform current density. The situation can also be improved by fixing the electrodes in position so that they cannot move relative to the heart. Pacing leads have been found to become fixed in position by fibrotic encapsulation in the first two weeks and measurements made before this process is completed are suspect. In fact, we have noted that about half the amplitude of impedance signals acquired immediately after implant is a result of lead motion and unrelated to ventricular volume.

The application of impedance plethysmography is additionally difficult when the goal is to make measurements in dilated hearts. Because of the large volume of these hearts (up to five or even ten times that of a normal heart) the average measured impedance is very low. In addition, the ejection fraction of these hearts may be as low as five percent resulting in a very small absolute change in impedance during the cardiac cycle. Thus, the signal/noise ratio in these patients is much worse than for patients with normal hearts. The baseline impedance, which follows the equation: $Z = \rho \cdot L^2 / V$ (where $\rho$ is the resistivity of the blood, L is the distance between sensing electrodes and V is the chamber volume) can be increased by increasing the inter-electrode distance, L with significant improvement in signal/noise ratio.

The subject of this application is an impedance plethysmography system to meet the multiple requirements of an implantable system. These requirements are that it 1) utilize simple and, if possible, standard leads and not require leads in addition to those necessary for therapy application, 2) measure left ventricular cardiac function, 3) be relatively immune to motion of the heart permitting accurate measurement from the time of system implant and be usable in dilated chambers, such as those in patients with moderate to severe heart failure, with inherently poor signal/noise ratio.

SUMMARY OF THE INVENTION

The invention is based on the utilization of at least one electrode on a coronary sinus/vein lead positioned in an anterior or posterior vein of the left ventricle and electrodes on pacing or defibrillation leads position in the right ventricle and/or right atrium. The coronary vein lead may be positioned for pacing in a distal portion of a coronary vein and may be combined with a right ventricular or right atrial lead to span the left ventricular blood volume. A high frequency current source and sensing amplifier may be connected to electrodes available on these leads in a number of ways to measure electrical impedance. In each of these configurations, the sensing electrodes span some region of the left ventricle and would, therefore, be sensitive to left ventricular volume and wall motion.

This arrangement meets all the requirements outlined previously. It does not require leads or electrodes in addition to those necessary for pacing or defibrillation therapy. It is primarily sensitive to left ventricular function and because the coronary vein electrode has very limited motion (being confined to the inner diameter of the distal portion of a coronary vein), is relatively free of lead motion artifact. Finally, the ability to increase the distance between sensing electrodes by choosing distant combinations of electrodes improves the signal-to-noise ratio in dilated hearts.

DESCRIPTION OF THE DRAWINGS

The foregoing features, objects and advantages will become apparent to those skilled in the art from the following detailed description of a preferred embodiment especially when considered in conjunction with the accompanying drawings in which.

DESCRIPTION OF THE PREFERRED EMBODIMENT

Figure 1:
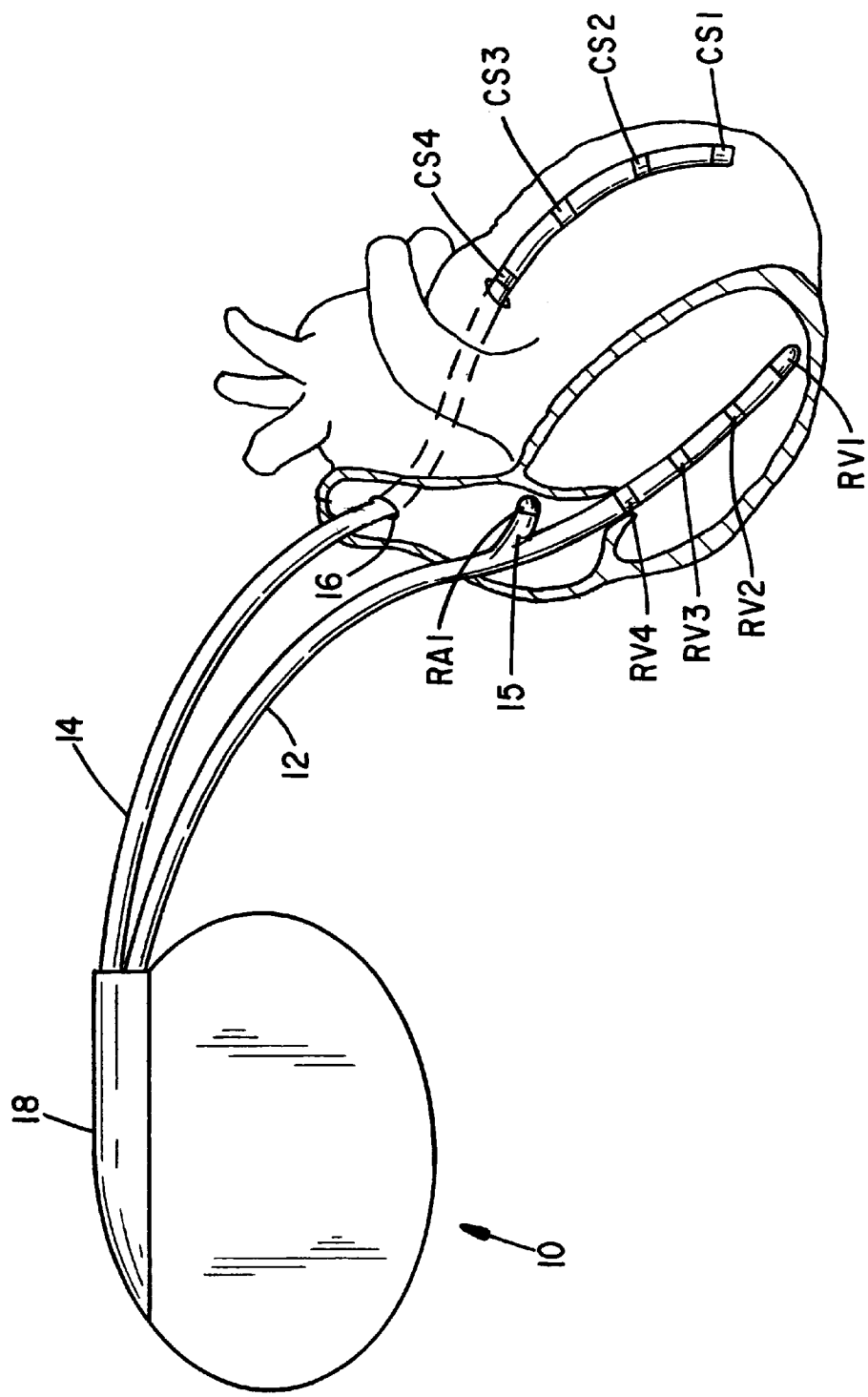
FIG. 1 diagrammatically depicts a heart having multiple-electrode right ventricular and coronary sinus leads coupled to a cardiac rhythm management device.

Referring first to FIG. 1, there is indicated generally by numeral 10 a cardiac rhythm management device which may, typically, comprise a cardiac pacemaker, and/or a defibrillator that would be implantable within a patient. Alternatively, the device 10 may be an external unit for use in acute studies for diagnostic purposes. In this specification, the device 10 will be considered to be designed to apply electrical stimulation therapy for congestive heart failure and to monitor the cardiac output to permit optimization of the pacing site or the relative timing (AV delay) between the sensing of an atrial depolarization signal and electrical stimulation of the left (and possibly right) ventricle. This is done by periodically changing the pacing site, e.g., by pacing at a different coronary vein electrode, or by changing the AV delay and monitoring the evoked change in cardiac output to determine whether it increases or decreases. This procedure can be continued until the cardiac output is maximized.

The device 10 is shown as being connected to a right ventricular lead 12 having two electrodes labeled RV1 and RV2. While two electrodes are illustrated, it should be understood that a greater or fewer number may be employed on the lead 12. A coronary sinus lead 14 is shown as entering the coronary sinus 16 in the right atrium and extending therethrough and into a vein traversing the myocardium on the left side of the heart. The coronary sinus lead 14 is illustrated as having a plurality of electrodes CS1 through CS4 on a surface thereof and connected by individual conductors within the lead 14 to circuitry within the device 10. Again, while four such electrodes are shown, it is only for the purpose of illustration and, typically, a fewer number of electrodes would be placed on the CS lead 14 because of size constraints of the lumen in which the lead is to be placed. It is further contemplated that an additional lead 15 with an electrode RA1 may be positioned at a location abutting the right atrial wall of the heart. The atrial lead 15 may be a branch off the right atrial lead 12 and will include a conductor connecting RA1 to contacts within the connector 18 of the pacemaker device 10.

Figure 3:
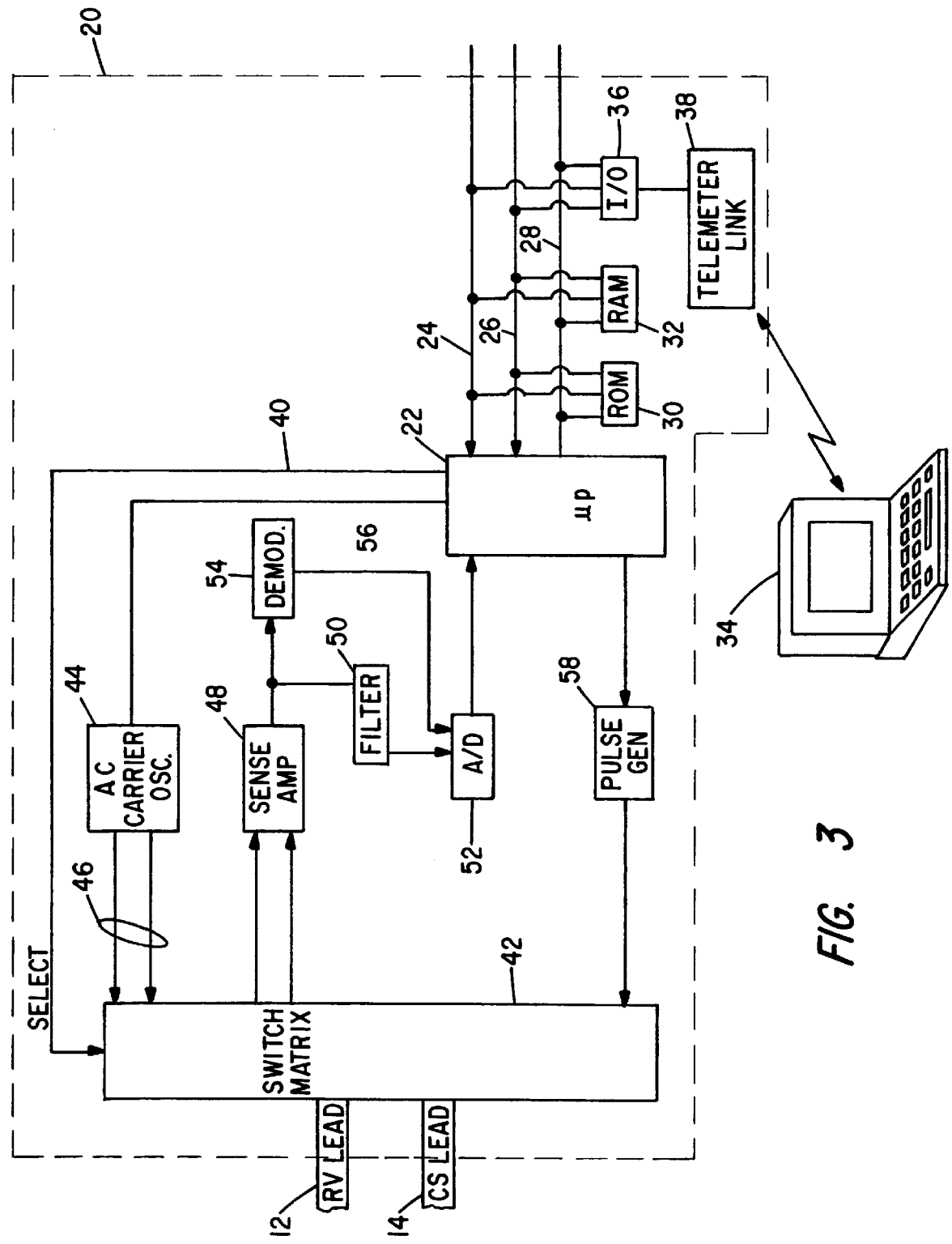
FIG. 3 is a schematic block diagram of the cardiac rhythm management device shown in FIG. 1.

Referring next to FIG. 3, the internal circuitry of the device 10 is shown as being enclosed in the dashed line box 20. It includes a microprocessor based controller 22. Connected to the microprocessor 22 is an address bus 24, a data bus 26 and a control bus 28. Connected to each of these buses is a ROM memory 30 storing a program of instructions executable by the microprocessor 22 for carrying out the control functions yet to be described. Also connected to the buses 24, 26 and 28 is a RAM memory 32 which may store various control parameters called upon by the microprocessor 22 during execution of its program. The RAM 32 may also store data resulting from computations for later read-out to an external monitor 34, via I/O circuit 36 and a telemetry link 38. Of course, data and programmable parameters may also be entered into the implanted unit, via the external monitor, the telemetry link and the I/O module 36.

The microprocessor-based controller 22 is connected by a control line 40 to a "select" input of a switching matrix 42 whereby selected ones of the several electrodes RV1, RV2, CS1-CS4 and RA1 may be selected to function either as a drive electrode or a sense electrode. A hard-wired connection may also be used.

In implementing impedance plethysmography, an oscillator circuit 44 is provided. It, too, is controlled by a microprocessor 22 to produce an AC carrier signal on lines 46 whose amplitude is below that which is required to evoke capture (depolarization) of the heart and whose frequency may be typically 5–10 KHz. The switch matrix 42 permits the carrier signal to be applied across a selected pair of electrodes on the leads 12, 14 and 15. Likewise, a selected pair of these electrodes, preferably not used for applying the carrier signal, may be selected to function as sensing electrodes and they are connected, via the switch matrix 42, to a sense amplifier 48.

As those skilled in the art appreciate, the application of the AC carrier signal across a pair of electrodes creates an electric field and since blood is a fairly good conductor, the inflow and outflow of blood from the heart results in a change in impedance and, therefore, the voltage being picked up by the selected pair of sensing electrodes. The output from the sense amplifier 48 may be suitably filtered, as at 50, to remove the high frequency carrier component of the composite signal picked up by the sense amplifier, thereby leaving the ECG waveform. This waveform may be digitized by an analog-to-digital converter 52 and applied to the microprocessor-based controller 22 as a digital quantity. The composite signal from the sense amplifier 48 may also be applied to a demodulator circuit 54 whereby the modulation envelope is separated from the carrier, such that an impedance vs. time waveform is delivered over line 56 to the A/D converter 52. Once digitized, the impedance signal can be further signal processed, such as by first smoothing the waveform using a 6-point moving window, then windowing on a beat-to-beat basis with a fiducial point selectively chosen to focus on a predetermined portion of the cardiac cycle of interest. Ensemble averaging may also prove effective in emphasizing a particular feature of the impedance waveform. This further signal processing can be carried out in the analog domain, but preferably in the digital domain within the microprocessor 22.

As is explained in the aforereferenced Salo et al. patent, a signal proportional to cardiac output can be derived from the impedance vs. time signal and the cardiac output signal can, in turn, be used to optimize the pacing site or AV delay in a CHF therapy device or pacing rate in a rate adaptive cardiac rhythm management device.

The microprocessor 22 also controls a pulse generator 58 that is used to apply cardiac stimulating pulses to the heart via selected electrodes on one or the other of the leads 12, 14 and 15. The particular electrodes, again, are selected by the microprocessor 22 controlling the switch matrix 42.

By locating electrodes on the left side of the heart, via the coronary sinus/vein lead, the electric field created by the impedance sensing circuitry can be localized in the left ventricle, resulting in improved measurement of left ventricle stroke volume, determination of ejection fraction, rate of filling and a measure of the amount of mitral valve regurgitation present. The ability to select the site where impedance sensing takes place will also afford a way of timing different cardiac features for diagnostic or control purposes.

Figure 2A:
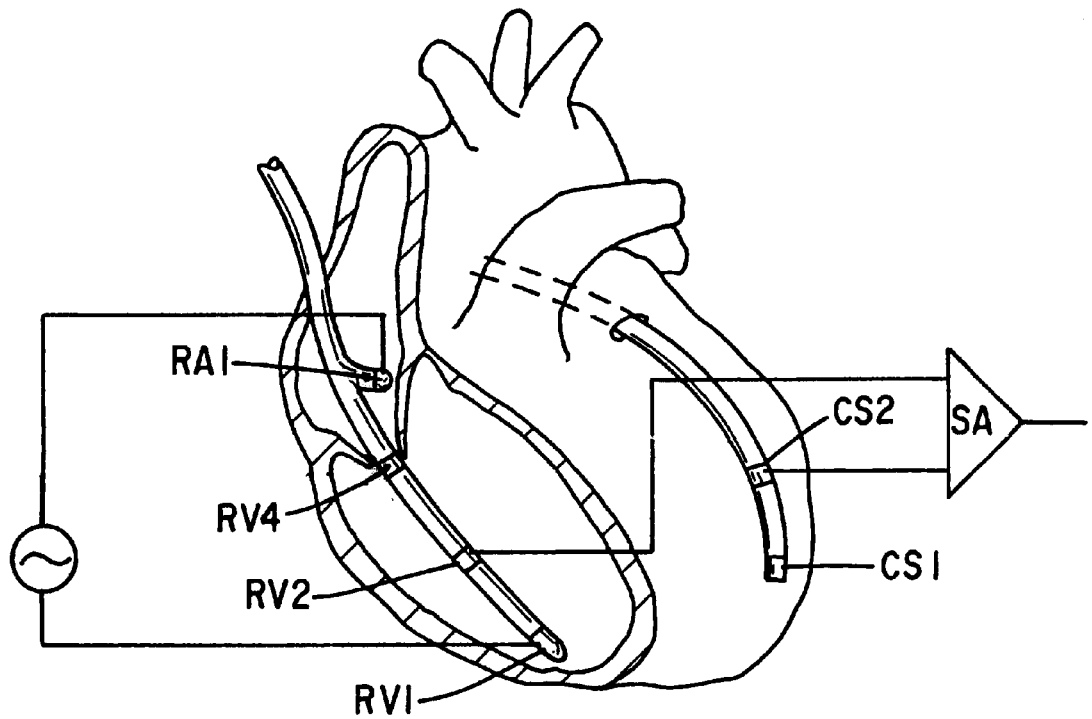
FIGS. 2A, 2B, 2C, 2D and 2E schematically display drive and sense electrode combinations for measuring electrical impedance utilizing coronary vein, right ventricular and right atrial electrodes, each combination showing differing sensitivities to desired cardiac parameters, such as left ventricular volume and timing of ejection and filling.

Studies using the present invention have shown that if the AC carrier signal is applied between electrodes RV1 and RA1 and with the sense amplifier connected to electrodes RV2 and CS2 as in FIG. 2(a), timing features of the cardiac cycle, e.g., the time of the beginning of ejection, can be determined. This arrangement also affords the additional advantage that only one electrode would be required on the coronary sinus lead which translates to a relatively small outside diameter of the lead for placement in a myocardial vein on the left side of the heart. Alternatively, if electrodes RV1 and RV2 are used for the current sources and with the sense signal picked up between electrodes CS2 and CS3, as in FIG. 2(b), changes in left ventricular volume are enhanced. Here again, only two electrodes would be required on the coronary sinus lead which also portends a small diameter configuration.

It is also contemplated that the drive source can be connected across electrodes CS1 and CS4 and with sensing across electrodes CS2 and CS3. See FIG. 2(c). While this configuration requires four electrodes, both stroke volume and timing features peculiar to the left ventricle can be more readily derived than when driving and sensing both occur in the right ventricle. Since four electrodes are required to implement this configuration, it may prove best for acute studies only. Such acute studies can be used to determine which configuration is best for a particular patient and then chronic leads having only the number of electrodes needed to achieve the optimum results need be chronically implanted.

Figure 2B:
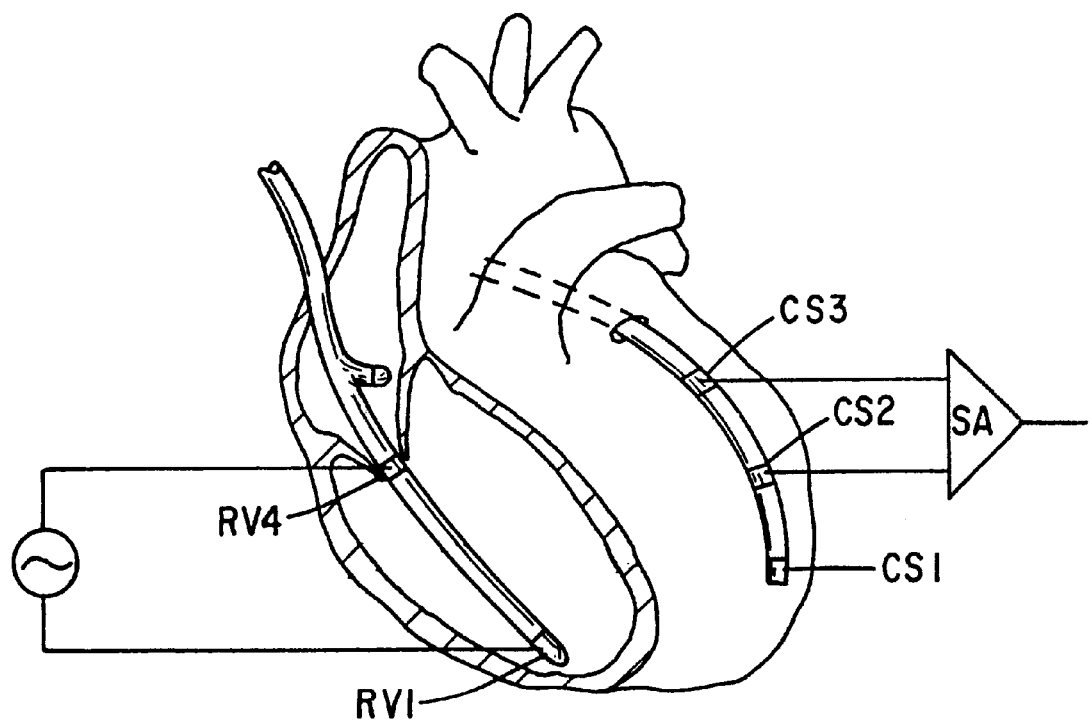
Figure 2C:
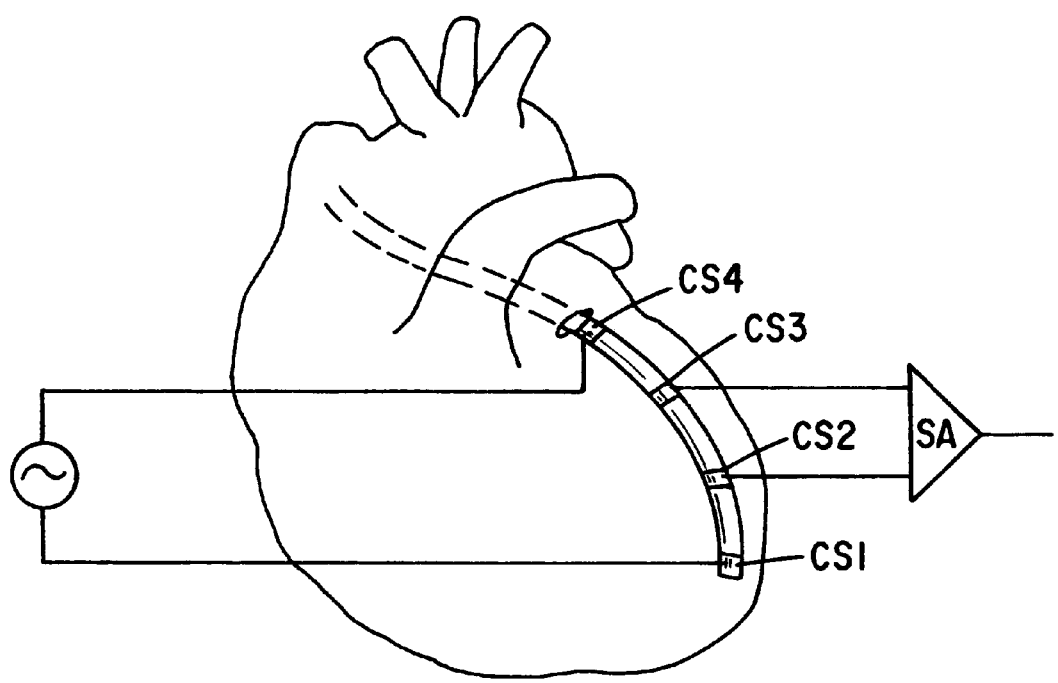
Figure 2D:
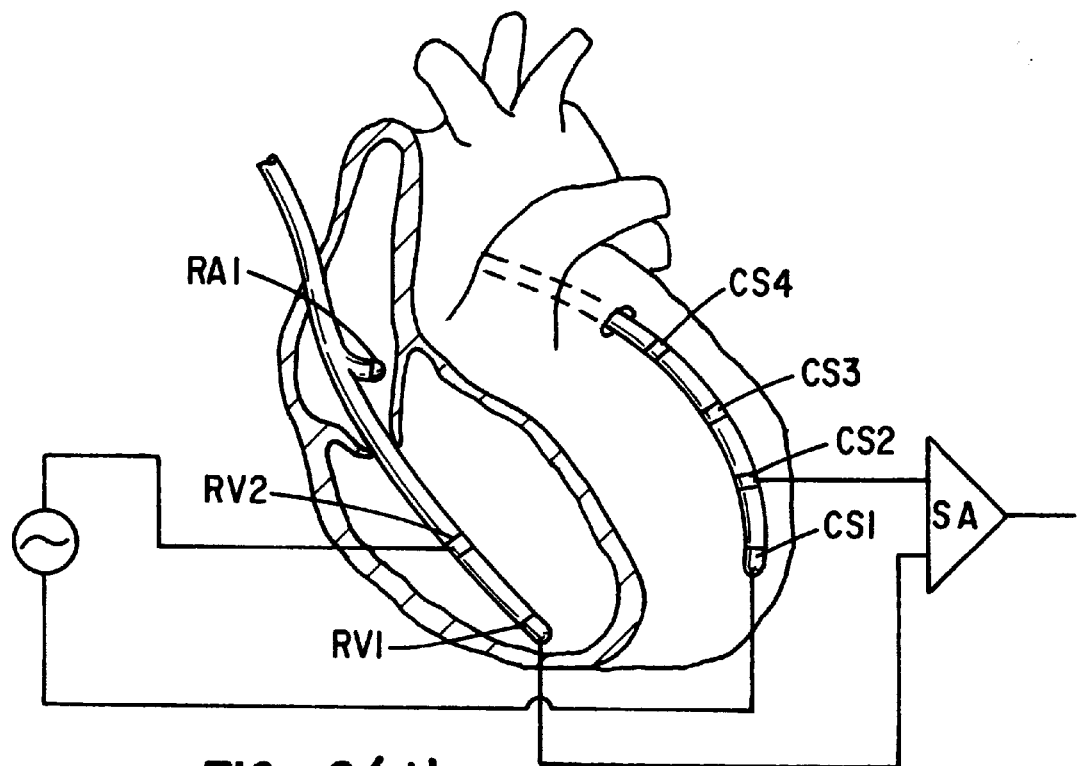

It is also possible to measure interchamber impedance with the configuration shown in FIG. 2(d). In this arrangement, the current (drive) source is connected to one of at least two electrodes on the coronary sinus/vein lead and to one of the at least two electrodes on the right ventricular lead. The sense amplifier is connected to one of the other electrodes on the coronary sinus lead and to one of the other electrodes on the right ventricular lead. This configuration requires only two bipolar (two electrode) leads and, since the sensing electrodes span the left ventricle, is sensitive to ventricular volume and wall motion.

Figure 2E:
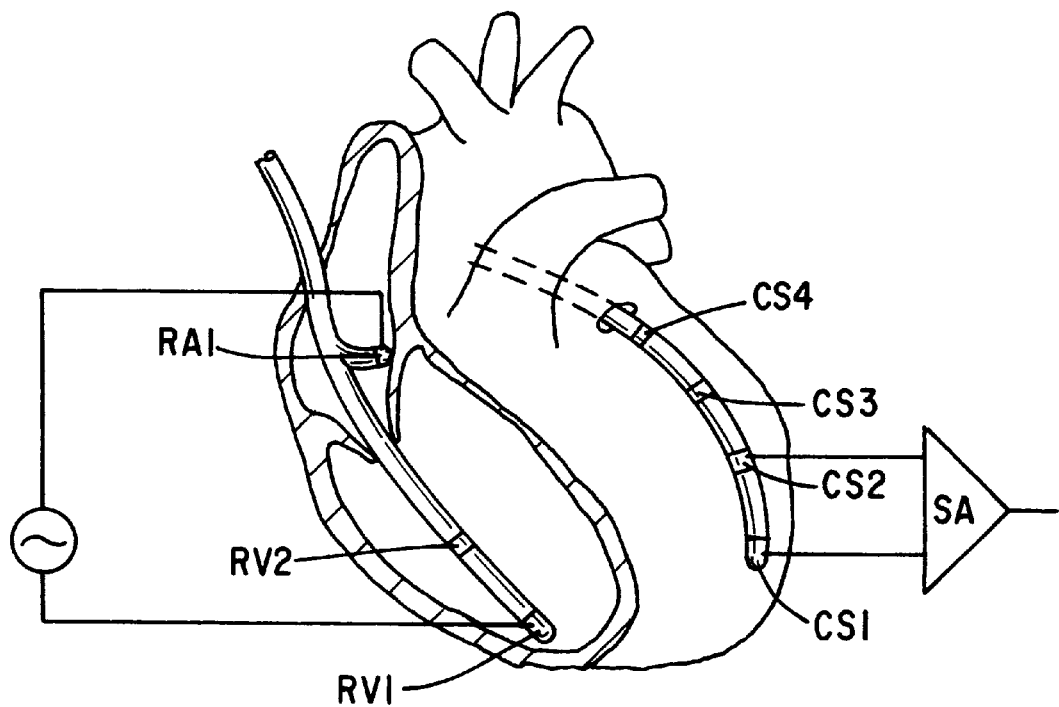

Another measurement of chamber impedance can be generated by the configuration shown in FIG. 2(e). In this arrangement, the current source is connected to an electrode in the right atrium and to an electrode in the right ventricle. The electrical potential field generated by the current source is detected by a sense amplifier connected to two electrodes on a lead in a coronary vein. This configuration is similar to that of FIG. 2(b), but requires only unipolar (single electrode) leads in the right ventricle and right atrium. This arrangement like that of FIG. 2(b) is most useful for following changes in left ventricular wall thickness and for extracting timing information from wall thickness changes.

The use of a left coronary vein lead in conjunction with other sites in the right ventricular cardiac chamber has been found to greatly improve the ability of impedance plethysmography to sense both timing and volume features in the cardiac cycle. Given the mechanical constraint imposed on the lead by the coronary vein, motion artifacts are significantly reduced. Configurations incorporating electrodes on both the coronary vein lead and the right ventricular lead permit the measurement of impedances between different chambers and also along different current paths. This makes it possible to select combinations with improved signal-to-noise ratio to significantly improve the quality of the impedance measurement.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of carrying out impedance plethysmography on a living heart, comprising the steps of:
   (a) installing a first lead having a plurality of electrodes in a right ventricular chamber of said living heart;
   (b) installing a second lead having a plurality of electrodes in a coronary vein on the left ventricle of said heart;
   (c) coupling a subthreshold AC drive signal between selected ones of the electrodes on the first and second leads;
   (d) coupling a signal sensing circuit between at least one electrode on the second lead and another selected one of the electrodes on one of the first and second leads; and
   (e) extracting a signal representative of electrical impedance from the signal sensing circuit.

2. A method for carrying out impedance plethysmography on a living heart, comprising the steps of:
   (a) installing a first lead including at least two electrodes in a right ventricular chamber of said heart;
   (b) installing a second lead including a plurality of electrodes in a coronary vein on the left ventricle of the heart;
   (c) coupling a subthreshold AC drive signal source between one of
      (i) the at least two electrodes on the first lead,
      (ii) one of the at least two electrodes on the first lead and a first of the plurality of electrodes on the second lead,
      (iii) the first and a second of the plurality of electrodes on the second lead;
   (d) coupling a signal sensing circuit between
      (i) a third and a fourth electrode on the second lead when the AC drive signal is coupled to the at least two electrodes on the first lead,
      (ii) the other of the at least two electrodes on the first lead and the first of the plurality of the electrodes on the second lead when the AC drive signal is coupled to one of the at least two electrodes on the first lead and the third of the plurality of electrodes on the second lead,
      (iii) the third and fourth of the plurality of electrodes on the second lead when the AC drive signal is coupled to the first and second of the plurality of electrodes on the second lead; and (e) extracting a signal representative of electrical impedance from the signal sensing circuit.

3. A method for carrying out impedance plethysmography comprising the steps of:
  (a) installing a first lead including at least two electrodes in a right ventricular chamber of said heart;
  (b) installing a second lead including a plurality of electrodes in a coronary vein on the left ventricle of the heart;
  (c) installing a third lead having an electrode in a right atrial chamber of the heart;
  (d) coupling an AC drive signal source between one of:
    (i) the at least two electrodes on the first lead,
    (ii) one of the at least two electrodes on the first lead and a first of the plurality of electrodes on the second lead,
    (iii) the first and a second of the plurality of electrodes on the second lead,
    (iv) the electrode on the third lead and one of the electrodes on the first lead;
  (e) coupling a signal sensing circuit between:
    (i) a third and a fourth of the plurality of electrodes on the second lead when the AC drive signal is coupled to the at least two electrodes on the first lead,
    (ii) the other of the at least two electrodes on the first lead and the third of the plurality of electrodes on the second lead when the AC drive signal is coupled to one of the at least two electrodes on the first lead and a third of the plurality of electrodes on the second lead,
    (iii) the third and a fourth of the plurality of electrodes on the second lead when the AC drive signal is coupled to the first and second of the plurality of electrodes on the second lead,
    (iv) the first and the third of the plurality of electrodes on the second lead or the other electrode on the first lead and the third of the plurality of electrodes on the second lead when the AC drive signal is coupled to the electrode on the third lead and one of the electrodes on the first lead; and
  (f) extracting a signal representative of the electrical impedance from the signal sensing circuit.

4. A method for carrying out impedance plethysmography on a living heart, comprising the steps of:
  (a) installing a first lead in a right ventricle of the heart, the first lead including at least two electrodes $RV_1$ and $RV_2$ thereon disposed in the right ventricle;
  (b) installing a second lead in a coronary vein on the left ventricle of the heart, the second lead including a plurality of electrodes including at least two of $CS_1$, $CS_2$, $CS_3$ and $CS_4$ thereon;
  (c) coupling a source of subthreshold AC drive signals and a signal sensing circuit to predetermined pairs of said electrodes in accordance with an entry in the following table:

| AC DRIVE SOURCE | SENSING CIRCUIT |
|---|---|
| $RV_1$, $RV_2$ | $CS_2$, $CS_3$ |
| $CS_1$, $CS_4$ | $CS_2$, $CS_3$ |
| $RV_2$, $CS_1$ | $RV_1$, $CS_2$ | and;
  (d) extracting a signal representative of electrical impedance from the signal sensing circuit.

5. The method of claim 4 and further including the steps of:
  (a) installing a third lead in a right atrial chamber, the third lead including an electrode $RA_1$ thereon; and
  (b) coupling the source of subthreshold AC drive signals and the sensing circuit to predetermined pairs of said electrodes in accordance with an entry in the following table:

| AC Drive Source | Sensing Circuit |
|---|---|
| $RA_1$, $RV_1$ | $RV_2$, $CS_2$ |
| $RA_1$, $RV_1$ | $CS_1$, $CS_2$ |
| $RV_1$, $RV_2$ | $CS_2$, $CS_3$ |
| $CS_1$, $CS_4$ | $CS_2$, $CS_3$ |
| $RV_2$, $CS_1$ | $RV_1$, $CS_2$ |

6. An apparatus for conducting impedance plethysmography on a living heart, comprising:
  (a) a first electrical lead having a plurality of electrodes adapted for placement in a coronary vein on the left ventricular chamber of said heart;
  (b) a second lead having a plurality of electrodes and adapted for placement in a right ventricular chamber of the heart;
  (c) means for applying a subthreshold AC carrier signal across selected ones of said plurality of electrodes on one or both of the first and second electrical leads;
  (d) means for sensing electrical signals connected across a pair of said plurality of electrodes where at least one of said pair of electrodes is on the first electrical lead; and
  (e) means connected to the sensing means for demodulating the sensed electrical signals.

7. Apparatus for carrying out impedance plethysmography on a living heart, comprising:
  (a) a first lead having a plurality of electrodes adapted for placement in a right ventricular chamber of said heart;
  (b) a second lead having a plurality of electrodes adapted for placement in a coronary vein on the left ventricle of the heart;
  (c) a source of AC drive signals;
  (d) a switching circuit for connecting said source of AC drive signals to selected ones of the electrodes on the first and second leads;
  (e) a signal sensing circuit coupled by the switching circuit to at least one electrode on the second lead and another electrode on the second lead and another electrode on one of the first and second leads; and
  (f) a demodulator coupled to the signal sensing circuit, the demodulator extracting a signal proportional to the electrical impedance between said at least one electrode on the second lead and said another electrode on one of the first and second leads.

8. An apparatus for carrying out impedance plethysmography on a living heart, comprising:
  (a) a first electrical lead having at least two electrodes thereon adapted for placement in the right ventricular chamber of said heart;
  (b) a second electrical lead having a plurality of electrodes thereon adapted for placement in a coronary vein on the left ventricle of said heart;
  (c) a source of AC drive signals;

(d) a signal sensing circuit;
(e) a switching circuit for connecting said source and said sensing circuit to the electrodes on the first and second leads in accordance with an entry in the following table:

| AC DRIVE SOURCE | SENSING CIRCUIT | FIGURE |
|---|---|---|
| $RV_1$, $RV_4$ | $CS_2$, $CS_3$ | 2b |
| $CS_1$, $CS_4$ | $CS_2$, $CS_3$ | 2c |
| $RV_2$, $CS_1$ | $RV_1$, $CS_2$ | 2d | and;
(f) a demodulator coupled to the signal sensing circuit, the demodulator extracting a signal proportional to the electrical impedance between the electrodes to which the switching circuit has connected the sensing circuit.

9. The apparatus of claim 8 and further including:

(a) a third lead adapted for placement in the right atrium of the heart, the third lead including an electrode $RA_1$ thereon; said switching circuit connecting said source and said sensing circuit to the electrodes on the first, second and third leads in accordance with an entry in the following table:

| RA DRIVE SOURCE | SENSING CIRCUIT | FIGURE |
|---|---|---|
| $RA_1$, $RV_1$ | $RV_2$, $CS_2$ | 2a |
| $RA_1$, $RV_1$ | $CS_1$, $CS_2$ | 2e |

\* \* \* \* \*

UNITED STATES PATENT AND TRADEMARK OFFICE
CERTIFICATE OF CORRECTION

PATENT NO. : 6,278,894 B1
DATED : August 21, 2001
INVENTOR(S) : Rodney W. Salo, V.A. Kadhiresan and Kevin G. Nugent It is certified that error appears in the above-identified patent and that said Letters Patent is hereby corrected as shown below:

<u>Column 10,</u>
Line 10, delete "RA" and insert -- "AC" --.

Signed and Sealed this

Thirtieth Day of April, 2002

*Attest:*

*Attesting Officer*

JAMES E. ROGAN
*Director of the United States Patent and Trademark Office*